United States Patent [19]

Freenor, III et al.

[11] 4,123,255
[45] Oct. 31, 1978

[54] O-SULFONYL-ALPHA-CYANO 2,6-DIHALOBENZALDOXIMES

[75] Inventors: Francis J. Freenor, III, Richmond; Barbara M. Koerber, Berkeley, both of Calif.

[73] Assignee: Chevron Research Company, San Francisco, Calif.

[21] Appl. No.: 756,566

[22] Filed: Jan. 3, 1977

[51] Int. Cl.² .................. A01N 9/14; C07C 121/66
[52] U.S. Cl. .................................. 71/103; 260/465 E
[58] Field of Search ............... 71/103, 121; 260/465 E

[56] References Cited

U.S. PATENT DOCUMENTS

| 3,165,392 | 1/1965 | Koopman | 71/106 |
| 3,234,255 | 2/1966 | Hackmann el al. | 71/103 |
| 3,717,690 | 2/1973 | Newman | 71/103 |
| 3,752,661 | 8/1973 | Orlett | 71/103 |
| 3,896,155 | 7/1975 | Hamprecht el al. | 71/103 |
| 4,009,192 | 2/1977 | Fischer el al. | 71/103 |

*Primary Examiner*—Glennon H. Hollrah
*Attorney, Agent, or Firm*—Dix A. Newell; T. G. DeJonghe; Raymond Owyang

[57] ABSTRACT

O-alkylsulfonyl-, O-haloalkylsulfonyl- and O-dialkylaminosulfonyl-alpha-cyano-2,6-dihalobenzaldoximes are active pre-emergent herbicides.

19 Claims, No Drawings

O-SULFONYL-ALPHA-CYANO 2,6-DIHALOBENZALDOXIMES

BACKGROUND OF THE INVENTION

U.S. Pat. Nos. 3,165,392; 3,223,733; 3,234,255; 3,483,246; 3,495,968; 3,549,702 and 3,575,972 disclose pesticidal benzaldoximes, e.g., alpha-cyano-2,6-dichlorobenzaldoxime and alpha,2,6-trichlorobenzaldoxime.

DESCRIPTION OF THE INVENTION

The herbicidal benzaldoximes of the invention are represented by the formula (I)

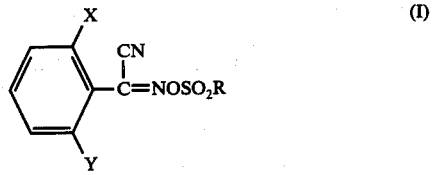

wherein R is alkyl of 1 to 4 carbon atoms; haloalkyl of 1 to 4 carbon atoms and of 1 to 5 fluoro, chloro, bromo or iodo; or dialkylamino of 2 to 6 carbon atoms, X is chloro or bromo and Y is chloro or bromo.

Representative alkyl R groups include methyl, ethyl, propyl, sec-butyl, etc. Representative haloalkyl R groups include fluoromethyl, chloromethyl, iodomethyl, dibromomethyl, trichloromethyl, 2-chloroethyl, pentachloroethyl, 2,2,2-trichloroethyl, 3-chloropropyl, 4-bromobutyl, etc. Representative dialkylamino R groups include dimethylamino, ethylmethylamino, dipropylamino, etc.

Preferably R is alkyl of 1 to 3 carbon atoms or haloalkyl of 1 to 2 carbon atoms and 1 to 3 fluoro, chloro or bromo groups; and X and Y are chloro.

Representative benzaldoxime esters of the invention are O-methylsulfonyl-alpha-cyano-2,6-dichlorobenzaldoxime, O-isopropylsulfonyl-alpha-cyano-2-chloro-6-bromobenzaldoxime, O-fluoromethylsulfonyl-alpha-cyano-2,6-dichlorobenzaldoxime, O-dichloromethylsulfonyl-alpha-cyano-2,6-dichlorobenzaldoxime, O-(2-bromoethylsulfonyl)-alpha-cyano-2-chloro-6-bromobenzaldoxime, O-(1,1,2,2-tetrachloroethylsulfonyl)-alpha-cyano-2,6-dibromobenzaldoxime and O-diethylaminosulfonyl-alpha-cyano-2,6-dibromobenzaldoxime.

The alpha-cyanobenzaldoximes of the invention can exist as syn- or anti-isomers or as mixtures thereof and the present invention relates to any or all of these forms. However, it has been found that the higher melting isomer generally is more herbicidally active. Although it is not known with certainty, it is believed the higher melting isomer is the anti-isomer.

The compounds of the invention are prepared by reacting an alpha-cyano-2,6-dihalobenzaldoxime or its alkali metal salt, e.g., sodium or potassium, with a sulfonyl chloride compound of the formula $RSO_2Cl$ wherein R has the same significance as previously defined. Generally, the reaction is conducted by reacting substantially equimolar amounts of the alpha-cyano-2,6-dihalobenzaldoxime (or alkali metal salt) and the sulfonyl chloride in an inert diluent at a temperature of 0° to 100° C. When alpha-cyano-2,6-dihalobenzaldoxime is employed as the reactant, it is generally convenient to employ an acid acceptor. Suitable acid acceptors are organic amines such as pyridene compounds, e.g., pyridine or alpha-picoline, and lower trialkylamines, e.g., triethylamine or tripropylamine, and alkali metal carbonates, e.g., sodium carbonate. Generally, at least one mol of acid acceptor is employed for each mol of sulfonyl chloride.

The product (I) is isolated and purified by conventional procedures such as extraction, filtration, crystallization and chromatography. The product (I) is generally a mixture of the syn- and anti-isomers. However, the pure anti- or syn-isomers can be obtained by crystallization or chromatography.

EXAMPLES

EXAMPLE 1

Preparation of O-dimethyl amino-alpha-cyano-2,6-dichlorobenzaldoxime

A mixture of 5.3 g (0.025 mol) alpha-cyano-2,6-dichlorobenzaldoxime (U.S. Pat. No. 3,234,255), 3.6 g (0.025 mol) dimethylaminosulfonyl chloride and 10 g (0.1 mol) sodium carbonate in 75 ml dimethoxyethane was heated under reflux for 2 hours. After standing overnight, the reaction mixture was filtered and evaporated under reduced pressure to give a yellow oil which crystallized on standing. Recrystallization from ether/benzene gave the product as yellow solid, m.p. 107–108. Nuclear magnetic resonance analysis showed the product to be approximately a 60:40 mixture of the syn- and anti-isomers. Elemental analysis for the product is tabulated in Table I under Compound No. 1.

EXAMPLE 2

Preparation of O-methyl sulfonyl-alpha-cyano-2,6-dichlorobenzaldoxime

A 3.3 g (0.028 mol) sample of methylsulfonyl chloride was added slowly to a slurry of 6.5 g (0.027 mol) of the sodium salt of alpha-cyano-2,6-dichlorobenzaldoxime in 60 ml acetone. The reaction was exothermic. After the addition was completed, the reaction mixture was stirred at about 25° C. for 1 hour, filtered and evaporated under reduced pressure to give a tan oil which crystallized to give the product. Recrystallization from ether/hexane gave the product as white crystals, m.p. 81–82. Nuclear magnetic resonance analysis showed the product to be approximately a 60:40 mixture of the syn- and anti-isomers. Elemental analysis for the product is tabulated in Table I as Compound No 3.

A sample of product (mixture of syn- and anti-isomers) was separated by crystallization from a solvent mixture of isopropyl alcohol/hexane/ether to give one isomer melting at 109°–110° C. and a second isomer melting at 117°–118° C. The lower melting isomer is tabulated in Table I as Compound No. 15 and the higher melting isomer is tabulated in Table I as Compound No. 17.

EXAMPLE 3

Preparation of O-3-chloro-propylsulfonyl-alpha-cyano-2,6-dichlorobenzaldoxime

A 5.0 g (0.0281 mol) sample of 3-chloropropylsulfonyl chloride was added slowly at about 0° C. (ice bath) to a suspension of 6.7 g (0.0281 mol) of the sodium salt of alpha-cyano-2,6-dichlorobenzaldoxime in 60 ml benzene. The reaction was exothermic. The reaction mixture was stirred at 25° C. for 2 hours during which time a solid product formed. The reaction mixture was then diluted with 200 ml dichloromethane, washed with water, dried over magnesium sulfate and silica gel, and evaporated under reduced pressure to give a yellow oil. The oil was crystallized from ether/hexane to give the product as white crystals, m.p. 86°-88° C. This product is tabulated in Table I as compound No. 12.

A second crop of white crystals, melting at 69°-75° C., was obtained from the mother liquor. This product is tabulated in Table I as compound No. 28.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are most effective when applied pre-emergently.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type control. Generally for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 mcg/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

TABLE I

Compounds of the formula 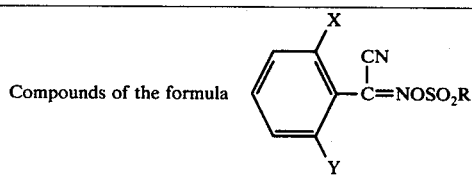

| No. | X,Y | R | Melting Point, °C | Sulfur Calc. | Sulfur Found | Chlorine Calc. | Chlorine Found |
|---|---|---|---|---|---|---|---|
| 1 | Cl,Cl | N(CH$_3$)$_2$ | 69 | 10.0 | 9.5 | 22.0 | 21.2 |
| 2* | " | CH$_2$Cl | 107–108 | 9.8 | 9.9 | 32.5 | 27.8 |
| 3 | " | CH$_3$ | 81–82 | 10.9 | 11.0 | 24.2 | 24.4 |
| 4 | " | n-C$_3$H$_7$ | 98–100 | 10.0 | 10.4 | 22.1 | 21.8 |
| 5 | " | CH$_2$Cl | 73–79 | 9.8 | 10.0 | 32.5 | 31.4 |
| 6 | " | CF$_3$ | Oil | 9.2 | 9.9 | 20.4 | 19.4 |
| 7* | " | i-C$_3$H$_7$ | 86 | 10.0 | 10.2 | 22.1 | 21.4 |
| 8 | " | i-C$_3$H$_7$ | 56–58 | 10.0 | 10.1 | 22.1 | 22.8 |
| 9 | " | C$_2$H$_5$ | 78 | 10.4 | 9.8 | 23.1 | 19.7 |
| 10* | " | CH$_2$CH$_2$Cl | 101 | 9.4 | 9.6 | 31.1 | 30.6 |
| 11 | " | CHClCH$_3$ | 90–93 | 9.4 | 9.6 | 31.1 | 30.4 |
| 12* | " | CH$_2$CH$_2$CH$_2$Cl | 86–88 | 9.0 | 9.3 | 29.9 | 29.4 |
| 13 | " | CH$_2$Br | 84–87 | | | 8.17** | 7.7 |
| 14 | " | sec-C$_4$H$_9$ | Oil | 9.6 | 10.3 | 21.2 | 22.3 |
| 15* | " | CH$_3$ | 109–110 | 10.9 | 11.0 | 24.2 | 24.2 |
| 16* | " | i-C$_4$H$_9$ | 93 | 9.6 | 9.9 | 21.2 | 21.6 |
| 17* | " | CH$_3$ | 117–118 | 10.9 | 11.0 | 24.2 | 24.3 |
| 18 | " | CH$_2$CH$_2$CH$_2$CH$_2$Cl | 68–69 | 8.7 | 8.7 | 28.8 | 29.8 |
| 19 | Cl,Br | CH$_3$ | 116–117 | 9.5 | 9.7 | 5.9 | 6.1 |
| 20 | " | CH$_2$CH$_2$CH$_2$Cl | 100–103 | 8.0 | 8.7 | 7.5** | 7.4 |
| 21 | " | CH$_2$Br | 123–125 | 7.7 | 8.0 | 7.2** | 7.0 |
| 22 | " | N(CH$_3$)$_2$ | 82–86 | 8.8 | 8.4 | 5.4** | 4.3 |
| 23 | " | CF$_3$ | Oil | 8.2 | 7.8 | 5.1** | 5.0 |

TABLE I-continued

Compounds of the formula 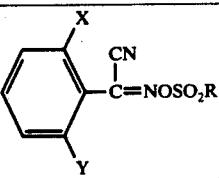

| No. | X,Y | R | Melting Point, °C | Sulfur Calc. | Sulfur Found | Chlorine Calc. | Chlorine Found |
|---|---|---|---|---|---|---|---|
| 24 | " | i-$C_3H_7$ | 85–86 | 8.8 | 8.0 | 5.5** | 5.1 |
| 25 | " | $C_2H_5$ | 53–58 | 9.1 | 8.6 | 5.7** | 5.5 |
| 26 | " | $CH_2Cl$ | 69–72 | 8.6 | 8.8 | 8.1** | 7.8 |
| 27 | Cl,Cl | $CH_2CH_2Cl$ | 76–78 | 9.4 | 9.9 | 31.1 | 30.2 |
| 28 | " | $CH_2CH_2CH_2Cl$ | 69–75 | 9.0 | 8.5 | 29.9 | 28.3 |

*essentially pure syn or anti-isomer  
**total halogen

TABLE II

| Compound No. | O | W | C | M | P | L |
|---|---|---|---|---|---|---|
| 1 | 90 | 30 | 20 | 20 | 20 | 100 |
| 2 | 100 | 25 | 10 | 95 | 100 | 100 |
| 3 | 100 | 87 | 95 | 90 | 100 | 100 |
| 4 | 85 | 40 | 50 | 0 | 75 | 75 |
| 5 | 100 | 95 | 85 | 85 | 100 | 100 |
| 6 | 88 | 10 | 15 | 70 | 75 | 100 |
| 7 | 100 | 95 | 98 | 100 | 100 | 100 |
| 8 | 100 | 100 | 98 | 95 | 100 | 100 |
| 9 | 90 | 70 | 70 | 50 | 88 | 100 |
| 10 | 85 | 0 | 0 | 0 | 90 | 100 |
| 11 | 100 | 83 | 95 | 30 | 50 | 100 |
| 12 | 95 | 70 | 70 | 80 | 100 | 100 |
| 13 | 100 | 75 | 50 | 60 | 100 | 100 |
| 14 | 80 | 45 | 30 | 60 | 75 | 100 |
| 15 | 55 | 40 | 45 | 15 | 35 | — |
| 16 | 65 | 20 | 65 | 0 | 0 | 0 |
| 17 | 85 | 95 | 83 | 100 | 100 | 100 |
| 18 | 60 | 30 | — | 40 | 65 | 100 |
| 19 | 100 | 0 | 15 | 0 | 10 | 100 |
| 20 | 100 | 50 | 70 | 0 | 95 | 100 |
| 21 | 95 | 80 | 75 | 100 | 100 | 100 |
| 22 | 0 | 0 | 0 | 0 | 0 | 100 |
| 23 | 70 | 65 | 0 | 100 | 60 | 100 |
| 24 | 100 | 100 | 100 | 90 | 100 | 100 |
| 25 | 60 | 100 | 100 | 50 | 100 | 100 |
| 26 | 100 | 15 | 0 | 70 | 100 | 100 |
| 27[4] | 2 | 10 | 23 | 10 | 47 | 95 |
| 28[4] | 99 | 100 | 98 | 99 | 100 | 100 |
| 29[1] | 0 | 0 | 0 | 0 | 0 | 0 |
| 30[2] | 0 | 0 | 0 | 0 | 0 | 0 |
| 31[3] | 0 | 0 | 0 | 0 | 0 | 0 |

[1] α-cyano-2,6-dichlorobenzaldoxime  
[2] o-methylsulfonyl-α-amino-2,6-dichlorobenzaldoxime  
[3] o-methylsulfonyl-α-dimethylamino-2,6-dichloro-benzaldoxime  
[4] tested at 100 micrograms/cm²  
O = Wild Oats (*Avena fatua*)  
W = Watergrass (*Echinochloa crusgalli*)  
C = Crabgrass (*Digitaria sanguinalis*)  
M = Mustard (*Brassica arvensis*)  
P = Pigweed (*Amaranthus retroflexus*)  
L = Lambsquarter (*Chenopodium album*)

What is claimed is:

1. A compound of the formula

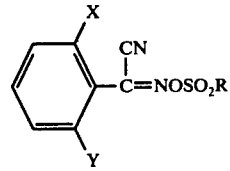

wherein R is alkyl of 1 to 4 carbon atoms, haloalkyl of 1 to 4 carbon atoms and of 1 fluoro, chloro, bromo or iodo, or dialkylamino of 2 to 6 carbon atoms, X is chloro or bromo and Y is chloro or bromo.

2. The compound of claim 1 wherein R is alkyl.

3. The compound of claim 1 wherein R is methyl, and X and Y are chloro.

4. The compound of claim 1 wherein R is haloalkyl.

5. The compound of claim 1 wherein R is haloalkyl of 1 to 2 carbon atoms and 1 fluoro, chloro or bromo, and X and Y are chloro.

6. The compound of claim 1 wherein R is dialkylamino.

7. A method for the control of undesirable vegetation which comprises applying thereto a herbicidally effective amount of the compound defined in claim 1.

8. The method of claim 7 wherein R is alkyl.

9. The method of claim 7 wherein R is methyl, and X and Y are chloro.

10. The method of claim 7 wherein R is haloalkyl.

11. The method of claim 7 wherein R is haloalkyl of 1 to 2 carbon atoms and 1 fluoro, chloro or bromo, and X and Y are chloro.

12. The method of claim 7 wherein R is dialkylamino.

13. The method of claim 1 wherein the compound is applied pre-emergently.

14. A herbicidal composition comprising a biologically inert carrier and a herbicidally effective amount of the compound of claim 1.

15. The composition of claim 14 wherein R is alkyl.

16. The composition of claim 14 wherein R is methyl, and X and Y are chloro.

17. The composition of claim 14 wherein R is haloalkyl.

18. The composition of claim 14 wherein R is haloalkyl of 1 to 2 carbon atoms and 1 fluoro, chloro or bromo, and X and Y are chloro.

19. The composition of claim 14 wherein R is dialkylamino.

* * * * *